United States Patent
Carden et al.

(10) Patent No.: US 9,512,317 B2
(45) Date of Patent: *Dec. 6, 2016

(54) METHOD FOR MANUFACTURING COLORING CERAMICS VIA COLLOIDAL DISPERSION FOLLOWED BY CONVENTIONAL PRESSING TECHNIQUES

(71) Applicant: James R. Glidewell Dental Ceramics, Inc., Newport Beach, CA (US)

(72) Inventors: Robin A. Carden, San Juan Capistrano, CA (US); Thomas C. Valenti, Rancho Santa Margarita, CA (US); Frank A. Jimenez, Santa Ana, CA (US)

(73) Assignee: James R. Glidwell Dental Ceramics, Inc., Newport Beach, CA (US)

( * ) Notice: Subject to any disclaimer, the term of this patent is extended or adjusted under 35 U.S.C. 154(b) by 1006 days.

This patent is subject to a terminal disclaimer.

(21) Appl. No.: 13/659,209

(22) Filed: Oct. 24, 2012

(65) Prior Publication Data

US 2014/0109797 A1    Apr. 24, 2014

Related U.S. Application Data

(63) Continuation-in-part of application No. 13/410,251, filed on Mar. 1, 2012.

(51) Int. Cl.
*A61K 6/02* (2006.01)
*C09C 1/34* (2006.01)

(52) U.S. Cl.
CPC ..................... *C09C 1/34* (2013.01)

(58) Field of Classification Search
CPC .................................................. A61K 6/024
USPC .................................. 264/16; 501/134, 152
See application file for complete search history.

(56) References Cited

U.S. PATENT DOCUMENTS

| | | |
|---|---|---|
| 4,557,691 A | 12/1985 | Martin |
| 6,709,694 B1 | 3/2004 | Suttor et al. |
| 2002/0081269 A1 | 6/2002 | Trom et al. |
| 2008/0303181 A1 | 12/2008 | Holand et al. |
| 2009/0042167 A1 | 2/2009 | Van Der Zel |
| 2010/0062398 A1 | 3/2010 | Schechner et al. |
| 2010/0221683 A1 | 9/2010 | Franke et al. |
| 2011/0151411 A1 | 6/2011 | Schechner et al. |
| 2014/0178834 A1 | 6/2014 | Jahns et al. |

FOREIGN PATENT DOCUMENTS

| | | |
|---|---|---|
| DE | 19619165 C1 | 9/1997 |
| WO | WO2013022612 A1 | 2/2013 |

OTHER PUBLICATIONS

International Search Report issued in PCT/US13/27951 dated Jun. 17, 2013.
International Search Report issued in PCT/US13/27961 dated Jun. 28, 2013.

*Primary Examiner* — David Sorkin
(74) *Attorney, Agent, or Firm* — Dianne Burkhard

(57) ABSTRACT

A colored ceramic powder is produced from a mixture of coloring solutions consisting of metallic salts that are introduced to a ceramic slurry and subsequently dried. The coloring solution may comprise for example of chosen metallic salts, a solvent, an organic solvent such as derivatives of propylene oxides, an acid and a possible binder. Once all the constituents are thoroughly mixed to a homogeneous state, the slip is dried to a powder form, which spray drying equipment can be used. The dried powder can then be subjected to an isostatic or biaxial press manufacturing process to create a green state ceramic body. Once pressed, the ceramic body can be subjected to a sintering process. After final sinter, the resulting ceramic body possesses an innate color that is homogenous throughout its composition. The method is especially useful for coloring zirconia dental restorations.

30 Claims, No Drawings

METHOD FOR MANUFACTURING COLORING CERAMICS VIA COLLOIDAL DISPERSION FOLLOWED BY CONVENTIONAL PRESSING TECHNIQUES

CROSS-REFERENCE TO RELATED APPLICATIONS

This application is a continuation-in-part of application Ser. No. 13/410,251 filed on Mar. 1, 2012.

BACKGROUND OF THE INVENTION

Field of the Invention

The present invention relates to the process in which a color solution consisting of metallic salts is introduced to a ceramic slurry and subsequently combined with a binder, dried, pressed into a green state and sintered.

Background Art

Current techniques for coloring ceramics have limitations due to processing. At present, methods involve dipping a pre-sintered ceramic body into a coloring solution containing metallic salts. Such methods may often result in inhomogeneous coloring on the surface of the ceramic. In addition, the penetration of the coloring solution into the pores of the ceramic is largely affected by the components, composition, and properties of the solution. Depending on the constituents present in the solution, little or no color penetration can result.

Such disadvantages arise when attempting to color a pre-sintered ceramic. This has prompted the need for an alternative method to color a ceramic body. Such a method will remove the need to color a pre-sintered ceramic body and will result in a ceramic with innate color aesthetics that are homogenous throughout the ceramic both internally and on the surface. The present invention relates to creating a colored ceramic during a slip casting process in which a color solution consisting of metallic salts is introduced into the slip and subsequently combined with a binder, dried, pressed into a green state and sintered.

Current methods for coloring ceramic bodies involve dipping a pre-sintered ceramic of final shape into a coloring liquid. These processes require a wide range of soaking times and drying times to ensure uniform and good quality results. After dipping, the ceramic body is dried and sintered, after which the final color is achieved.

The dipping methods currently used depend largely on the capillary action of the coloring liquid and the infiltration of said liquid into ceramic pores. The properties of the coloring liquid, such as composition, concentration, viscosity, pH, surface tension and wetting ability directly influence the performance of the liquid. Should any property not be optimized, undesirable results such as disproportionate coloring or poor penetration of color into the ceramic body may result.

These methods color ceramic bodies after the ceramic has already been processed and fabricated. The coloring agent is added to the ceramic system after initial fabrication of the ceramic. Therefore, the color is not innate to the ceramic.

SUMMARY OF THE INVENTION

The present invention relates to a process for coloring ceramics by colloidal dispersion. It is during this slip casting that a coloring solution consisting of metallic salts is introduced to the slurry and subsequently combined with a binder, dried into a pressable colored powder, pressed into a green state and sintered.

A coloring solution may comprise for example a metallic salt, a solvent, an organic solvent such as derivatives of propylene oxides, and an acid can be introduced to the slip casting process.

Such a coloring solution can be added to the slip. The solution is thoroughly mixed with the ceramic slurry, after which the ceramic body is combined with a binder, dried and finally subjected to a sintering process.

After final sinter, the resulting ceramic body possesses an innate color that is homogenous throughout its composition.

The present invention utilizes metallic salts as the coloring agent present in the coloring liquid that is added to the slip. The primary property of the metallic salt is such that is soluble in the solvent.

Metallic salts of transition metals from groups 3-12 on the periodic table can be used for the coloring solution. In addition, salts from rare earth metals can be used as well. Metallic salts in the forms of oxides or containing anions such as: $Cl^-$, $SO_4^-$, $SO_3^-$, $Br^-$, $F^-$, $NO_2^-$, and $NO_3^-$ may be used.

The coloring solution, as it relates to the process by which a colored ceramic is made via colloidal dispersion, should contain metallic salts in the range of 0.01% to 5% by weight. The concentration of the metallic salts is directly dependent on the target color that is to be achieved.

A preferred coloring solution also contains an organic solvent. The purpose for this solvent is to assure the homogeneity of the solution that contains the metallic salts. Derivatives of polypropylene oxide can be used for this purpose.

The coloring solution, as it relates to the process by which a colored ceramic is made via a slip, should be comprised of an organic solvent of 1% to about 10% by weight and a binder of 0.5% to 10% by weight.

A preferred coloring solution also contains acid. The purpose of this component is to maintain the colloidal stability of the coloring solution when mixed into the ceramic slurry by upholding a stable pH. An acidic pH level in the range of 1.0 to 4.0 is ideal.

The coloring solution, as it relates to the process by which a colored ceramic is made via colloidal dispersion, should be comprised of an acid of 0.05% to about 5% by weight.

The primary property of the solvent is that it can dissolve the metallic salts and facilitate a homogenous solution. Solvents can include water, alcohols, ketones, organic solvents, or mixtures thereof. The solvent comprises the majority of the solution by weight.

The present invention encompasses the process by which the colored ceramic is fabricated. Due to the unique properties of color that includes hue, chroma and value, varying ratios of coloring liquid are added to the ceramic slurry before the slip casting process. The ratio is directly dependent on the target color that is to be achieved.

The colloidal slip, as it relates to the process by which a colored ceramic is made, should have a ratio of grams of coloring liquid per gram of ceramic slurry in a range of about 0.01 to about 1.00.

The present invention may be employed in the fabrication of a colored ceramic using a unique colloidal mixing process of a coloring agent into a ceramic slurry. The coloring liquid is added to the ceramic slurry and afterward mixed to assure that a homogenous mixture is attained. The slurry mixture is then combined with a binder, dried into a powder, pressed into a green state and sintered.

After final sinter, a homogeneously colored ceramic body results.

An object of this invention is to create a ceramic body with a color of specific hue, chroma, and value. A further object is to create a process that allows for a multitude of colors to be achieved.

Still a further object is to create a process that allows for the fabrication of a ceramic body with a homogeneous and uniform color without adverse effects on the mechanical and optical properties of the ceramic.

Still a further object is to create a coloring solution designed for the ceramic fabrication process that results in a uniformly colored ceramic.

DETAILED DESCRIPTION OF A PREFERRED EMBODIMENT

The present invention relates to color a ceramic body during the initial process and fabrication of the ceramic. A coloring solution is added to the ceramic system during the processing stage. The result is a ceramic with intrinsic color properties and complete color saturation.

A color solution of known compositions and concentrations can be used to create any color of desired hue, chroma and value. Using metallic salts as the coloring agent, as well as a solvent to disperse the salts into solution, this invention relates to a process that is designed for coloring a ceramic during the manufacturing process of the material.

The process hereof ensures total and homogeneous color penetration into a ceramic body. Such a ceramic body can then be cut or milled into any shape or form. The final sintered ceramic body will be colored completely without the need for an extra coloring process that normally takes hours using conventional ceramic color methods.

The coloring solution and process hereof do not adversely affect the mechanical and optical properties of the natural ceramic. Because the coloring agent is mixed in a colloidal process, the coloring ions are homogenously distributed through the ceramic's crystal structure. Therefore, the coloring ions are incorporated throughout the ceramic.

Application

The present invention relates to the fabrication of a colored ceramic using a unique colloidal mixing process of a coloring agent into a ceramic slurry. Such a process can be applied to the dental industry, particularly in the fabrication of dental zirconia. At present, zirconia blocks are fabricated for the milling of dental crowns, bridges and copings. Due to the natural strength and aesthetics of teeth, such mechanical and optical properties are needed in dental ceramics.

At present, dental frameworks are milled from zirconia blocks. Because the natural color of zirconia is white, there is a need to color the ceramic. The ceramic is therefore colored using conventional dipping methods using coloring liquids. Current methods involve dipping a pre-sintered zirconia framework of final shape into the color liquid for a specified soaking time period. Frameworks are subsequently dried and sintered. The dental industry at large uses the VITA classic shade guide as a standard for teeth aesthetics. These colors are unique in hue, chroma and value. Conventional color liquids are made to match these properties.

The present invention can eliminate the need for the coloring process of the pre-sintered dental frameworks. A zirconia dental ceramic can be fabricated with the innate color properties of the final desired product.

It is within the scope of the present invention to fabricate a dental zirconia ceramic with a color that matches the hue, chroma and value of the VITA Classic dental shades.

It is also within the scope of the present invention to fabricate a dental zirconia ceramic block that can be milled to a specified dental framework of final shape and subsequently sintered. The resulting sintered zirconia framework will be of final shape and color that matches the VITA Classic shades.

Testing Results

Successful results have been achieved with the present invention. A coloring solution of known concentration and composition and mixed it into a colloidal zirconia slurry was used.

A coloring solution containing $TbCl_3$, $CrCl_3$, propylene glycol, 37% hydrochloric acid and de-ionized water was added to a zirconia slurry.

The exact composition of the coloring solution is as follows; 0.0914 wt % $TbCl_3$, 0.0609 wt % $CrCl_3$, 2.070 wt % propylene glycol, and 0.104 wt % hydrochloric acid. The balance was de-ionized water. The final pH of the solution was measured to be 1.93.

A ratio of 0.0218 grams of coloring liquid per gram of zirconia slurry was blended into a homogeneous mixture.

The slurry was subsequently combined with a binder, dried and pressed. This was followed by a sintering process during which the discs were fired into a pre-sintered bisque stage. After final sinter, the colored ceramic was cut to assure complete color saturation.

Total and homogenous coloring of the ceramic block was achieved. Using a VITA Easyshade instrument, the color was checked to verify if a dental shade had indeed been matched. The final color matched closely to the VITA Classic shade B2.

A second test was performed to verify the results of the first. A coloring liquid of different composition and concentration was used for processing.

The exact composition of the coloring solution is as follows: 0.122 wt % $TbCl_3$, 0.081 wt % $CrCl_3$, 2.030 wt % propylene glycol, and 0.104 wt % hydrochloric acid. The balance was de-ionized water. The final pH of the solution was measured to be 1.96.

A ratio of 0.0218 grams of coloring liquid per gram of zirconia slurry was blended into a homogeneous mixture with a binder.

The slurry was subsequently dried and pressed into a disc shape. This was followed by a sintering process during which the discs were fired into a pre-sintered bisque stage. After final sinter, the colored ceramic was cut to assure complete color saturation.

Total and homogenous coloring of the ceramic block was achieved. Using a VITA Easyshade instrument, the color was checked to verify if dental shade had indeed been matched. The final color matched closely to the VITA Classic shade A1.

Therefore, it will be understood that the present invention, as it relates to a coloring liquid that is introduced to a colloidal process by which a colored ceramic is fabricated, has proven to be particularly useful in the dental industry to create a dental ceramic with intrinsic colors that match the desired aesthetics of dental frameworks.

It will now be appreciated that the present invention relates to a unique process for providing selected coloring of ceramic materials in pressing fabrication by introducing a coloring solution of metallic salts into the slurry. This invention is particularly applicable to the coloring of fabricated zirconia blocks for use as dental restorations such as full contour crowns, bridges and the like. While exemplary In the claims:

1. A method of coloring a ceramic material product that is fabricated using a colloidal mixing process to form a ceramic slurry which can be combined with a binder, then dried, pressed and sintered; the method comprising the steps of:
   a) forming a coloring solution consisting essentially of at least one metallic salt, a solvent, an organic solvent and an acid, the at least one metallic salt soluble in the solvent;
   b) choosing the relative constituents of the coloring solution to provide a selected color;
   c) choosing a relative amount of the coloring solution for an amount of a ceramic slurry to provide a selected color intensity;
   d) adding the coloring solution to the ceramic slurry;
   e) mixing the coloring solution and the ceramic slurry to homogeneously distribute the coloring solution throughout the ceramic slurry; and
   f) adding a binder of from 0.5% to 10% by weight of said coloring solution to a mixture of the coloring solution and the ceramic slurry.

2. The method recited in claim 1 wherein step a) comprises the step of selecting salts of transition metals from groups 3-12 of the periodic table.

3. The method recited in claim 1 wherein step a) comprises the step of selecting salts of rare earth metals.

4. The method recited in claim 1 wherein step a) comprises the step of selecting metallic salts containing anions selected from the group consisting of $Cl^-$, $SO_4^-$, $SO_3^-$, $Br^-$, $F^-$, $NO_2^-$, and $NO_3^-$.

5. The method recited in claim 1 wherein in step a) said metallic salts comprise 0.01% to 5% by weight of said coloring solution.

6. The method recited in claim 1 wherein in step a) said organic solvent comprises 1% to 10% by weight of said coloring solution.

7. The method recited in claim 1 wherein in step a) said acid is selected to provide a pH of 1.0 to 4.0 for said coloring solution.

8. The method recited in claim 1 wherein in step a) said acid comprises 0.05% to 5% by weight of said coloring solution.

9. The method recited in claim 1 wherein in step a) said solvent is selected from the group of solvents consisting of water, alcohols, ketones, organic solvents and mixtures thereof.

10. The method recited in claim 1 wherein in step d) said coloring solution is provided in a weight ratio of 1% up to 50% of the weight of said slurry.

11. The method recited in claim 1 wherein in step a) said organic solvent comprises a derivative of a propylene oxide.

12. The method recited in claim 1 wherein said ceramic material product is made predominantly of zirconia.

13. A method of coloring a dental ceramic product that is fabricated using a colloidal mixing process to form a ceramic slurry which can be combined with a binder, then dried, pressed and sintered; the method comprising the steps of:
   a) forming a coloring solution consisting essentially of at least one metallic salt, a solvent, an organic solvent and an acid, wherein the coloring solution contains an amount of metallic salts in a range of 0.01 to 5% by weight of the coloring solution, and the metallic salts comprise $TbCl_3$ and $CrCl_3$;
   b) choosing the relative constituents of the coloring solution to provide a selected color;
   c) choosing the relative amount of the coloring solution for an amount of a ceramic slurry to provide a selected color intensity;
   d) adding the coloring solution to the ceramic slurry and mixing to homogeneously distribute the coloring solution throughout the slurry; and
   e) adding a binder to the mixture of the coloring solution and the ceramic slurry.

14. The method recited in claim 13 wherein in step a) said organic solvent comprises 1% to 10% by weight of said coloring solution.

15. The method recited in claim 13 wherein the coloring solution comprises an acid that is selected to provide a pH of 1.0 to 4.0 for said coloring solution.

16. The method recited in claim 13 wherein in step a) said acid comprises 0.05% to 5% by weight of said coloring solution.

17. The method recited in claim 13 wherein in step a) said solvent is selected from the group of solvents consisting of water, alcohols, ketones, organic solvents and mixtures thereof.

18. The method recited in claim 13 wherein in step c) said coloring solution is provided in a weight ratio of 1% up to 50% of the weight of said slurry.

19. The method recited in claim 13 wherein in step a) said organic solvent comprises a derivative of a propylene oxide.

20. The method recited in claim 13 wherein said dental ceramic product is made predominantly of zirconia.

21. The method recited in claim 13 wherein said binder comprises 0.5% to 10% by weight of said coloring solution.

22. A method of forming a colored zirconia ceramic powder material for use in making a dental ceramic product comprising:
   a) obtaining a coloring solution consisting essentially of water, at least one metallic salt as a coloring agent, and optionally an organic solvent, and optionally an acid;
   b) choosing an amount of the coloring solution for an amount of a zirconia ceramic slurry to provide a selected color intensity in a sintered dental ceramic product made from a colored zirconia ceramic powder material;
   c) adding the amount of coloring solution to the amount of zirconia ceramic slurry to form a mixture of the zirconia ceramic slurry and the coloring solution;
   d) combining the mixture of step c) and a binder; and
   e) drying a mixture of the coloring solution, the zirconia ceramic slurry and the binder to form the colored zirconia ceramic powder material.

23. The method of claim 22, wherein the weight ratio of the coloring solution to the zirconia ceramic slurry is in the range of 1% up to 50% of the weight of the zirconia ceramic slurry.

24. The method of claim 22, comprising a metallic salt of a rare earth metal, a transition metal, or both.

25. The method of claim 22, comprising pressing the colored zirconia ceramic powder material to form a block.

26. The method of claim 22, wherein the binder comprises 0.5% to 10% by weight of the coloring solution.

27. The method of claim 22, wherein the at least one metallic salt of the coloring solution contains anions selected from the group consisting of $Cl^-$, $SO_4^-$, $SO_3^-$, $Br^-$, $F^-$, $NO_2^-$, and $NO_3^-$.

28. The method of claim 22, wherein the coloring solutions contains 0.01% to 5% by weight of the at least one metallic salt.

29. The method of claim 22, wherein the coloring solution comprises propylene glycol.

30. The method of claim 22, wherein the coloring solution has a pH level in the range of 1.0 to 4.0.

* * * * *